United States Patent [19]
Bestetti et al.

[11] Patent Number: 6,053,902
[45] Date of Patent: Apr. 25, 2000

[54] IMPLANTED BODY CATHETER

[75] Inventors: Gilberto Bestetti, Köniz; Thomas Frei, Lützelflüh; Andreas Reinmann, Bern, all of Switzerland

[73] Assignee: Disetronic Licensing AG, Burgdorf, Switzerland

[21] Appl. No.: 09/076,279

[22] Filed: May 12, 1998

[51] Int. Cl.[7] .................................................. A61M 25/00

[52] U.S. Cl. ..................... 604/523; 604/174; 604/500; 604/533

[58] Field of Search ............................... 604/93, 175, 174, 604/905, 264, 500, 533, 523

[56] References Cited

U.S. PATENT DOCUMENTS

| | | | |
|---|---|---|---|
| 4,122,858 | 10/1978 | Schiff | 604/533 |
| 4,693,707 | 9/1987 | Dye | 604/905 X |
| 4,770,188 | 9/1988 | Chikama | 604/93 X |
| 4,886,501 | 12/1989 | Johnson et al. | 604/93 |
| 5,306,255 | 4/1994 | Haindl . | |

FOREIGN PATENT DOCUMENTS 0302076   4/1987   European Pat. Off. .

*Primary Examiner*—John D. Yasko

[57] ABSTRACT

A tubular catheter for implantation in a tubular structure of a human or animal body, comprising a lumen, characterized in that the catheter comprises a minimum of one radial groove.

18 Claims, 2 Drawing Sheets

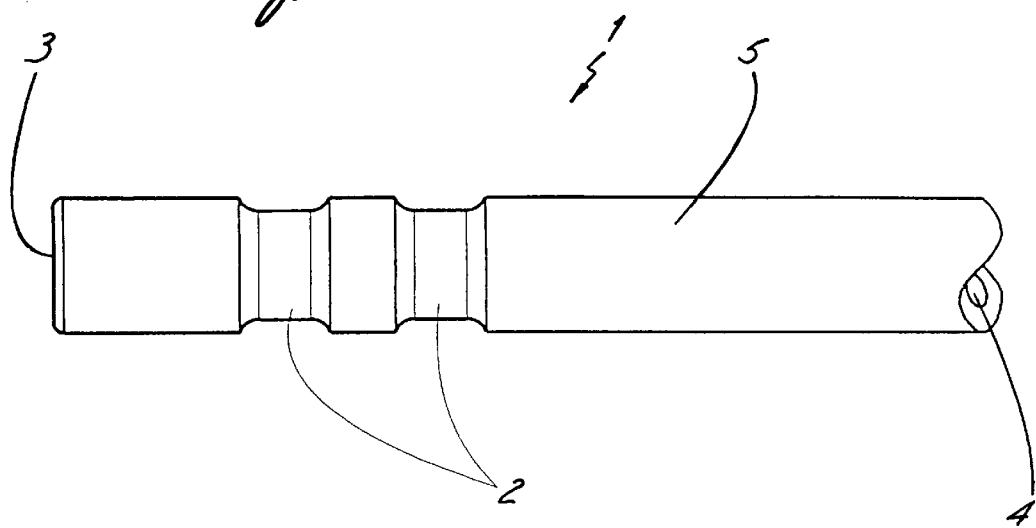
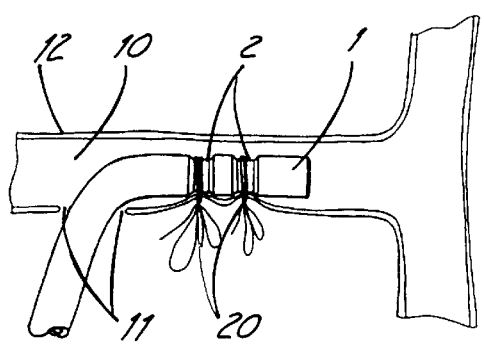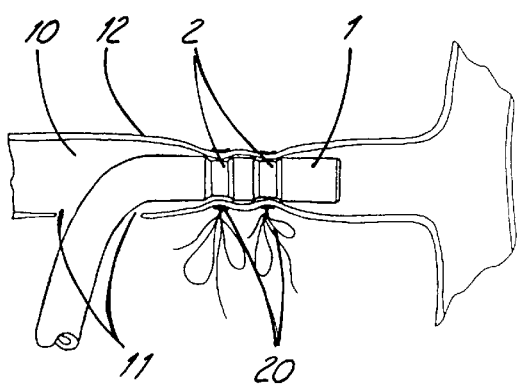

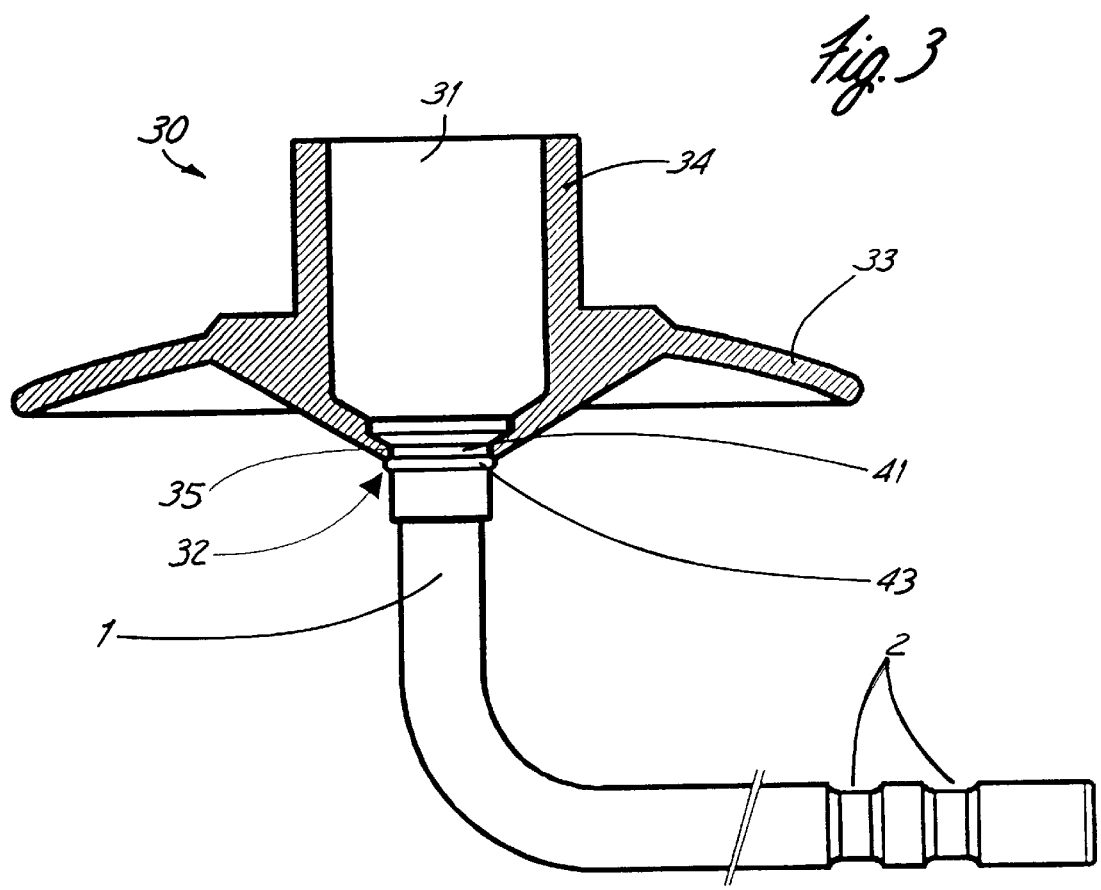

IMPLANTED BODY CATHETER

This application claims the priority of Swiss patent application 1239/97, filed May 27, 1997, which is incorporated herein by reference.

BACKGROUND OF THE INVENTION

Field of the Invention

This invention relates to a catheter to be implanted in a human or animal body in accordance with the preamble of claim 1.

SUMMARY

Catheters which normally remain in the body for an extended period of time for the introduction of drugs into human or animal blood vessels have been prior art for some time. the said catheters may be implanted in the body through the skin without a connector, thus allowing a single tube supplying a drug from a drug container to the site of release in the body. However, this constitutes a very high risk of infection. Consequently, a subcutaneous or percutaneous port unit is often arranged between a catheter implanted in the body and an infusion tub arranged outside the body, connecting the implanted catheter to the infusion tube. U.S. Pat. No. 5,206,255 describes a subcutaneously implanted port unit and patent specification EP-B-O 302 076 a percutaneously implanted port unit.

The arrangement of prior art implanted catheters in a blood vessel may cause tearing of the catheter from the vessel or rubbing of the catheter against the internal wall of the blood vessel or the point of entry of the catheter into a blood vessel unless the patient is restrained from moving.

The present invention intends to provide a remedy for this. The invention is based on the task of developing a catheter to be fixed for long-term implantation in a tubular structure of a human or animal body, having a lumen, such as a blood vessel, a lymphatic vessel or an umbilical vein, reducing the risks of being torn out and of infection without limiting a patient's freedom to move.

The invention solves the task by a catheter showing the features of claim 1.

The benefits offered by the invention are mainly due to the fact that the design of the catheter will increase the freedom of movement of the patient, while simultaneously reducing any tearing out and infection risks.

BRIEF DESCRIPTION OF THE DRAWINGS

A preferred example of the invention has been shown in the figures, where:

FIG. 1 is a catheter according to the invention.

FIG. 2a is a type of attachment of a catheter according to the invention.

FIG. 2b is a preferred type of attachment of a catheter according to the invention.

FIG. 3 is a type of coupling of the catheter according to the invention including a housing.

DETAILED DESCRIPTION

As shown in FIG. 1, the catheter 1 according to the invention comprises a cylindrical shaft 5, a continuous drug channel 4 provided in the interior of a catheter and an outlet 3. Two radial grooves 2 are arranged towards the outlet 3. From a production engineering point of view, the outlet 3 including the grooves 2 is attached by welding as a single accessory to an existing catheter 1. The external diameter of the outlet section 3 attached by welding should therefore be larger than the remaining tubular section of the catheter 1.

FIGS. 2a and 2b show that the catheter 1 is implanted in a tubular structure 10 comprising a lumen. The catheter 1 is inserted into the tubular wall 12 through an artificial opening 11. The tubular structure 10, for instance, is a still functioning blood or lymphatic vessel or a dried-up vessel, such as an umbilical vein. The catheter 1 is inserted into said tubular structure 10, followed by attachment with a biocompatible thread 20. As shown in FIG. 2b, the thread 20 is wrapped around the tubular structure 10 in a radial groove 2 of the catheter 1, thus allowing the thread 20 to press the tubular wall 12 into the radial groove 2.

However, the thread 20 may also be only partially wrapped around the tubular wall 12, as shown in FIG. 2a, and the tubular wall 12 may be pierced at a specific point, thus allowing the thread 20 within the tubular structure 10 to pass along the radial groove 2 and the press the tubular wall into the radial groove 2 outside the tubular structure 10. This offers the advantage that the lumen is not sealed.

In the embodiment shown, the catheter 1 comprises two radial grooves 2 for reasons of safety.

As shown in FIG. 3, the catheter 1 may be connected to a port unit 30 tapered towards the interior of the body. Such port units are used for connection of an infusion tube arranged outside a human or animal body to a catheter 1 located inside a human or animal body. The port unit 30 comprises a hollow cylindrical sleeve 34 and a radial anchoring plate 33 provided on the same. The port unit 30 comprises a first port 31 towards the exterior and a second port 32 towards the body interior. The second port 32 is at the tapered external end of the port unit 30. A sleeve edge 35 is formed by the second port 32 of the port unit.

In the preferred embodiment, the catheter 1 comprises a funnel-shaped catheter head 41 at the end opposite the outlet 3, with its base line showing a larger diameter than the second port 32 of the port unit 30. Below the catheter head 41, a radial rib 43 is provided, also having a diameter larger than the second port 32 of the port unit 30.

The catheter 1 is connected to the port unit 30, allowing the sleeve edge 35 of the port unit 30 to be located between the radial rib 43 of the catheter 1 and the catheter head 41. The funnel shape of the catheter head 41 allows the catheter head 41 to be wedged on the edge 35, thus eliminating movement of the catheter 1 towards the interior of the body, with the radial rib 43 preventing movement of the catheter 1 in the other direction.

In this constellation, the catheter 1 is either designed as a drug catheter or only as a guide catheter. The two types of catheters are different in that a guide catheter does not comprise a continuous drug channel 4 in its interior, but a channel 4 for the guidance of a drug catheter.

What is claimed is:

1. A tubular catheter for implanting in a tubular structure of a human or animal body, comprising a catheter body, having an outer surface, an inlet, an outlet, a lumen, and a minimum of one tie-down radial groove on the outer surface of the catheter adjacent to the outlet of the catheter for attaching the catheter to the tubular structure, whereby the tie-down radial groove allows at least a portion of the tubular structure to contact and be pressed into the groove by a biocompatible attachment.

2. A catheter in accordance with claim 1, wherein one or several grooves are arranged towards the outlet of the catheter.

3. A catheter in accordance with claim 1, wherein the catheter comprises a funnel-shaped head section provided opposite the outlet.

4. A catheter in accordance with claim 3, wherein a radial rib is provided below the head section.

5. A catheter according to claim 1, wherein the catheter is connectable to a port unit.

6. A catheter in accordance with claim 5, wherein the connection to the port unit is effected by wedging the funnel-shaped head section of the catheter to a sleeve edge formed by a port of the port unit.

7. A catheter according to claim 6, wherein the sleeve edge is located between the radial rib and the funnel-shaped head section of the catheter.

8. A catheter in accordance with claim 1, wherein the biocompatible means of attachment is a thread.

9. A catheter in accordance with claim 1, wherein an outlet section with the tie down radial groove is welded to the tubular catheter.

10. A catheter in accordance with claim 1, wherein attachment of the catheter is effected in a blood or lymphatic vessel or an umbilical vein.

11. A catheter for implanting in a tubular structure of a human or animal body, comprising:
 (a) a lumen extending between an inlet and an outlet of the catheter; and
 (b) at least one radial tie-down groove on the outer surface of the catheter adjacent to the outlet of the catheter for fastening the catheter to the tubular structure with a biocompatible attachment, whereby when the catheter is attached to the tubular structure, the at least one radial tie-down groove allows at least a portion of the tubular structure to be pressed directly into the at least one radial tie-down groove by a biocompatible attachment.

12. The catheter of claim 11, wherein two tie-down radial grooves are adjacent to the outlet of the catheter.

13. The catheter of claim 11, wherein the inlet to the catheter comprises a funnel-shaped head section and a radial rib adjacent the funnel-shaped head section.

14. The catheter of claim 13, wherein the catheter is connectable to a port unit by wedging the funnel-shaped head section to a sleeve edge formed on the port unit.

15. A catheter for long term implantation in a tubular structure of a human or animal body, comprising:
 (a) an elongated catheter body portion and an outlet end portion, said outlet end portion having an open outlet end; and
 (b) two circumferential tie-down grooves on the exterior surface of the outlet end portion of the catheter adjacent to the open outlet end for receiving at least a portion of a biocompatible thread attachment for fastening the outlet portion to and inside the tubular structure, at least a portion of the tubular structure is pressed directly into the grooves by the biocompatible thread attachment.

16. The catheter according to claim 15, wherein, when the catheter is fastened in the tubular structure, the tubular structure is pressed completely circumferentially into the grooves by the thread attachment.

17. A method for implanting a catheter in a tubular structure of a human or animal body, comprising:
 (a) providing a catheter having an elongated catheter body portion and an outlet end portion, said outlet end portion having an exterior surface and an open outlet end, and carrying at least one circumferential tie-down groove on the exterior surface of the catheter adjacent to the open outlet end;
 (b) inserting the outlet portion of the catheter into the tubular structure;
 (c) providing a biocompatible attachment; and
 (d) encircling the outlet portion of the catheter and at least a portion of the tubular structure with the biocompatible attachment generally at the tie-down grooves and tightening the attachment, whereby said at least a portion of the tubular structure is pressed into the tie-down groove thereby by fastening the outlet portion to and inside the tubular structure.

18. The method according to claim 17, wherein, when the outlet portion is fastened in the tubular structure, the tubular structure is pressed completely circumferentially into the at least one groove by the attachment.

* * * * *